United States Patent
Freimann

(10) Patent No.: US 11,426,067 B2
(45) Date of Patent: Aug. 30, 2022

(54) METHOD AND ASSEMBLY FOR ANALYSING THE WAVEFRONT EFFECT OF AN OPTICAL SYSTEM

(71) Applicant: Carl Zeiss SMT GmbH, Oberkochen (DE)

(72) Inventor: Rolf Freimann, Aalen (DE)

(73) Assignee: CARL ZEISS SMT GMBH, Oberkochen (DE)

( * ) Notice: Subject to any disclaimer, the term of this patent is extended or adjusted under 35 U.S.C. 154(b) by 286 days.

(21) Appl. No.: 16/830,880

(22) Filed: Mar. 26, 2020

(65) Prior Publication Data
US 2021/0022602 A1  Jan. 28, 2021

Related U.S. Application Data

(63) Continuation of application No. PCT/EP2018/075766, filed on Sep. 24, 2018.

(30) Foreign Application Priority Data

Sep. 27, 2017 (DE) ..................... 10 2017 217 251.7

(51) Int. Cl.
 *G01B 9/02* (2022.01)
 *A61B 3/10* (2006.01)
 (Continued)

(52) U.S. Cl.
 CPC .......... *A61B 3/1015* (2013.01); *A61B 3/0008* (2013.01); *G01B 9/02* (2013.01); *G03F 7/706* (2013.01)

(58) Field of Classification Search
 CPC .. G01B 9/02; G01J 9/02; G01J 9/0215; G03F 7/706; G01M 11/0271
 (Continued)

(56) References Cited

U.S. PATENT DOCUMENTS 6,438,199 B1  8/2002 Schultz et al.
7,768,653 B2  8/2010 Latypov et al.
(Continued)

FOREIGN PATENT DOCUMENTS

DE  10109929 A1  11/2001
DE  10053587 A1  5/2002
(Continued)

OTHER PUBLICATIONS

International Preliminary Report on Patentability, PCT/EP2018/075766, dated Mar. 31, 2020, 24 pages.
(Continued)

*Primary Examiner* — Md M Rahman
(74) *Attorney, Agent, or Firm* — Edell, Shapiro & Finnan, LLC

(57) ABSTRACT

A method for analyzing the wavefront effect of an optical system includes: illuminating a measurement mask (110, 310) with illumination light, producing an interferogram in a specified plane using a diffraction grating (150) from a wavefront from the illuminated measurement mask and traveling through the optical system; and capturing the interferogram with a detector (170). Different angular distributions of the illumination light incident on the measurement mask are produced via a mirror arrangement of independently settable mirror elements. A plurality of interferograms are captured in a plurality of measurement steps, wherein these measurement steps differ respectively in angular distribution of the illumination light that is incident on the measurement mask. A matching wavefront deviation portion in the measurement results obtained respectively in the measurement steps is ascertained to determine the respective system wavefront deviations of the optical system for the pupil regions illuminated respectively in the individual measurement steps.

20 Claims, 7 Drawing Sheets

(51) Int. Cl.
*A61B 3/00* (2006.01)
*G03F 7/20* (2006.01)

(58) Field of Classification Search
USPC .......................................................... 356/521
See application file for complete search history.

(56) References Cited

U.S. PATENT DOCUMENTS

| | | | |
|---|---|---|---|
| 8,559,108 B2 | 10/2013 | Kruizinga et al. | |
| 10,502,545 B2 | 12/2019 | Wegmann et al. | |
| 2002/0001088 A1 | 1/2002 | Wegmann et al. | |
| 2002/0136351 A1 | 9/2002 | Singer | |
| 2003/0043380 A1* | 3/2003 | Deck | G01B 9/02069 356/450 |
| 2005/0270511 A1 | 12/2005 | Dierichs et al. | |
| 2007/0223112 A1 | 9/2007 | Mann et al. | |
| 2011/0013171 A1 | 1/2011 | Mueller et al. | |
| 2014/0023835 A1 | 1/2014 | Freimann et al. | |
| 2014/0118712 A1 | 5/2014 | Goeppert et al. | |
| 2014/0191108 A1* | 7/2014 | Moriya | H05G 2/008 250/504 R |
| 2015/0009492 A1 | 1/2015 | Frese et al. | |
| 2015/0092174 A1* | 4/2015 | Endres | G02B 26/0833 359/359 |
| 2016/0202118 A1 | 7/2016 | Ehrmann et al. | |
| 2017/0336714 A1* | 11/2017 | Arnz | G03F 7/70266 |
| 2018/0087891 A1* | 3/2018 | Wegmann | G01M 11/0264 |
| 2018/0196350 A1 | 7/2018 | Bieling et al. | |

FOREIGN PATENT DOCUMENTS

| | | |
|---|---|---|
| DE | 102008004762 A1 | 7/2009 |
| DE | 102008000990 B3 | 11/2009 |
| DE | 102011005826 A1 | 3/2012 |
| DE | 102011077223 B4 | 8/2013 |
| DE | 102012204704 A1 | 9/2013 |
| DE | 102012209412 A1 | 12/2013 |
| DE | 102017200428 B3 | 6/2018 |
| DE | 102017217371 A1 | 4/2019 |
| DE | 102018204626 A1 | 4/2019 |
| EP | 1840622 A2 | 10/2007 |
| WO | 2015039751 A1 | 3/2015 |
| WO | 2016097048 A1 | 6/2016 |
| WO | 2016184571 A2 | 11/2016 |

OTHER PUBLICATIONS

GPTO Office Action with English translation, DE 10 2017 217 251, dated Jun. 7, 2018, 12 pages.
Wojdyla et al., "Ptychographic wavefront sensor for high-NA EUV inspection and exposure tools", Proc. of SPIE., vol. 9048, 2014, 5 pages.
International Search Report, PCT/EP2018/075766, dated Mar. 18, 2019, 7 pages.

* cited by examiner

METHOD AND ASSEMBLY FOR ANALYSING THE WAVEFRONT EFFECT OF AN OPTICAL SYSTEM

CROSS REFERENCE TO RELATED APPLICATIONS

This is a Continuation of International Application PCT/EP2018/075766, which has an international filing date of Sep. 24, 2018, and the disclosure of which is incorporated in its entirety into the present Continuation by reference. This Continuation also claims foreign priority under 35 U.S.C. § 119(a)-(d) to and also incorporates by reference, in its entirety, German Patent Application DE 10 2017 217 251.7 filed on Sep. 27, 2017.

FIELD OF THE INVENTION

The invention relates to a method and an arrangement for analyzing the wavefront effect of an optical system.

BACKGROUND

Microlithography is used for production of microstructured components, for example integrated circuits or LCDs. The microlithography process is conducted in what is called a projection exposure apparatus, which comprises an illumination device and a projection lens. The image of a mask (=reticle) illuminated by the illumination device is in this case projected by the projection lens onto a substrate (for example a silicon wafer) coated with a light-sensitive layer (photoresist) and arranged in the image plane of the projection lens, in order to transfer the mask structure to the light-sensitive coating of the substrate.

Both in the projection lens and in the illumination device there is a need to analyze the wavefronts propagating through the respective optical system during operation, in order e.g. to obtain information about the actually achieved optical effect of the individual optical components of the relevant optical system and the alignment thereof with respect to one another.

In this respect, the principle of shearing interferometry is known, inter alia, in which, through the use of a diffraction grating ("shearing grating"), which is placed in the region of the image plane of the imaging optical unit that is to be inspected in each case, identical copies of the wavefront to be measured are generated in accordance with the different orders of diffraction and are brought to superimposition. The light that is diffracted at this diffraction grating into different orders of diffraction produces, in a capturing plane that follows in the light propagation direction, an interference pattern, the evaluation of which permits, for example after resolution by way of a camera-based sensor, in principle a wavefront analysis and consequently allows for a conclusion to be drawn relating to the optical wavefront effect and any aberrations of the respective imaging optical unit and permits for example alignment of the optical components located in the imaging optical unit relative to one another.

It is known here to form the wavefront that has been coupled into the respective imaging optical unit by way of a coherence-shaping mask, which can be realized in particular such that exactly two orders of diffraction interfere with one another in the light propagation direction downstream of the shearing grating, whereas all other interferences are largely suppressed. In this way, disturbing interferences can be avoided and greater measurement accuracies can be attained.

It is furthermore known, for pupil filling, to either use spatial incoherence in the illumination (effected with diffuse light) in connection with a spatially extensive, shading (and "coherence shaping") mask or to provide the mask itself with scattering centers.

In order to avoid undesirable production of speckle patterns that accompany the above-described approaches based on a diffuser or scattering centers, it is furthermore known to attain dynamic pupil filling by realizing a scanning movement of the diffraction pattern, produced by the diffracting measurement mask, over the pupil by introducing an optical element that tilts the beam path. However, this results in an increase in the complexity of the structure and to increased equipment complexity e.g. owing to the introduction of additional optical elements for tilting the scattering cone and/or tilting the measurement mask itself.

For the prior art, reference is made merely by way of example to U.S. Pat. Nos. 7,768,653 B2, 8,559,108 B2, DE 101 09 929 A1 and DE 100 53 587 A1.

SUMMARY

Against the above background, it is an object of the present invention to provide a method and an arrangement for analyzing the wavefront effect of an optical system, which make possible the most accurate wavefront analysis with less equipment complexity. It is a further object to avoid the problems described above.

This object is achieved by the method and respectively the arrangement in accordance with the features of the independent patent claims.

A method according to the invention for analyzing the wavefront effect of an optical system includes the following steps:
 illuminating a measurement mask with illumination light by way of an illumination device;
 producing an interferogram in a specified plane using a diffraction grating from a wavefront that is coming from the measurement mask and travels through the optical system; and
 capturing this interferogram with a detector;
 wherein different angular distributions of the illumination light that is incident on the measurement mask are produced by a mirror arrangement of independently settable mirror elements;
 wherein a plurality of interferograms are captured in a plurality of measurement steps, wherein these measurement steps differ from one another in terms of the angular distribution of the illumination light that is incident on the measurement mask; and
 wherein a matching wavefront deviation portion in the measurement results obtained in each case in the measurement steps is ascertained to ascertain the respective system wavefront deviations of the optical system for the pupil regions illuminated in each case in said individual measurement steps.

Within the meaning of the present application, the "system wavefront" is understood to mean the wavefront that is produced when imaging a point light source through the optical system. The "system wavefront deviation" is the deviation of the system wavefront that converges into the image point produced by the optical system during the imaging from an ideal spherical wave. Furthermore, as will be described in more detail below, a wavefront deviation is decomposed according to the invention into a sum of summands, said summands being denoted "wavefront deviation portions."

Ultimately, systematic wavefront errors of the measurement arrangement can be ascertained in the sense of an "absolute calibration" or be separated from the actual system wavefront measurement using the method according to the invention, as will be explained in further detail below.

The invention is also based here in particular on the concept of illuminating a measurement mask, used to analyze the wavefront effect of an optical system, with a desired angular distribution that is variably settable and to avoid in this way the drawbacks described in the introductory part. In the respectively obtained measurement results or interferograms, undesirable speckle patterns can in particular be either avoided (owing to the configuration of the measurement mask without scattering centers) or be removed by calculation as part of the setting of different illumination settings during the illumination of the measurement mask. In addition, the increased equipment complexity associated in conventional approaches with moving or tilting the measurement mask can also be avoided by the invention.

A field facet mirror having a plurality of independently settable field facets, the use of which in combination with a pupil facet mirror in an illumination device for EUV operation (e.g. at wavelengths of less than 15 nm) is known for example from DE 100 53 587 A1, can be used component used for producing a desired angular distribution of the illumination light that is incident on the measurement mask. In further embodiments, the component used as part of the disclosure for producing a desired angular distribution can also be a diffractive optical element (DOE).

According to an embodiment of the method according to the invention, the beam direction of the illumination light that is incident on the mirror arrangement is varied over time to at least partially average out speckle patterns.

The optical system that is inspected according to the invention with respect to its wavefront effect can in particular be a projection lens of a microlithographic projection exposure apparatus.

According to an embodiment of the method according to the invention, the wavefront effect of the projection lens can be ascertained in a targeted fashion for the pupil regions that are illuminated during the operation of the projection exposure apparatus. A system wavefront deviation can be ascertained according to the invention in a manner such that, during the performance of the measurement, the illumination angular distribution that is set corresponds to the illumination angular distribution that is also used in the microlithography process.

In this way, it is possible to take account of the targeted illumination of specific pupil regions that typically takes place in the microlithography process, and the very system wavefront deviations that become effective in the microlithographic exposure can be captured in a targeted fashion. The system wavefront deviations can thus be ascertained—by way of a corresponding setting of the mirror arrangement of independently settable mirror elements—in the respective illumination setting that is also used in the microlithography process with the result that in particular thermally induced effects that arise or wavefront errors such as the heating of optical elements and aberrations associated therewith correspond to the effects or aberrations that then also occur in the microlithography process due to the concrete thermal load distribution within the projection lens.

In accordance with a further aspect, the invention also relates to a method for analyzing the wavefront effect of an optical system, wherein the method includes the following steps:

- illuminating a measurement mask with illumination light by way of an illumination device;
- producing an interferogram in a specified plane using a diffraction grating from a wavefront that is coming from the measurement mask and travels through the optical system; and
- capturing this interferogram with a detector;
- wherein different angular distributions of the illumination light that is incident on the measurement mask are producible by a mirror arrangement of independently settable mirror elements;
- wherein the optical system is a projection lens of a microlithographic projection exposure apparatus; and
- wherein the wavefront effect of the projection lens is ascertained in a targeted fashion by way of the setting of the mirror arrangement for the pupil regions which are illuminated during the operation of the projection exposure apparatus.

In accordance with an embodiment, the optical system is designed for operation at an operating wavelength of less than 30 nm, in particular less than 15 nm. The operating wavelength can here in particular have the values of 13.5 nm or 6.7 nm, which are currently typical in EUV lithography.

The invention furthermore also relates to an arrangement for analyzing the wavefront effect of an optical system, comprising

- an illumination device, having a field facet mirror with a plurality of field facets and having a pupil facet mirror with a plurality of pupil facets, wherein the field facets are independently adjustable to produce a desired angular distribution of the illumination light that is incident on the measurement mask;
- a measurement mask;
- a diffraction grating, which produces in each case an interferogram in a specified plane from in each case one wavefront which, during the illumination of the measurement mask with illumination light by way of the illumination device, is coming from the measurement mask and travels through the optical system for different angular distributions of the illumination light that is incident on the measurement mask;
- a detector for capturing the interferograms obtained for the different angular distributions of the illumination light that is incident on the measurement mask; and
- a calculation and storage unit for calculating and storing the respective system wavefront deviations of the optical system for the pupil regions that are respectively illuminated in the individual measurement steps, on the basis of a matching wavefront deviation portion in the interferograms obtained.

The disclosure also furthermore relates to an arrangement for analyzing the wavefront effect of an optical system, comprising

- an illumination device;
- a measurement mask;
- a diffraction grating, which produces at least one interferogram in a specified plane from a wavefront which, during the illumination of the measurement mask with illumination light by way of the illumination device, is coming from the measurement mask and travels through the optical system; and
- a detector for capturing said interferogram;

wherein the arrangement is configured to perform a method having the above-described features.

In embodiments, the arrangement furthermore has a device for varying the beam direction of the illumination light that is incident on the field facet mirror. Hereby, speckle patterns, which occur due to the spatial coherence of the incident light, can be at least partially averaged out as will be described below.

This aforementioned device for varying the beam direction can have for example a diffuser that is movable by rotation and/or translation (for randomly varying the beam direction). In further embodiments, the device can also have a beam direction control unit for the targeted (deterministic) control of the beam direction.

The aforementioned device for varying the beam direction can be arranged in particular in an intermediate focus located at the entrance of the illumination device or in the vicinity thereof.

The invention furthermore also relates to a microlithographic projection exposure apparatus, which is designed for operation at an operating wavelength of less than 30 nm and has an illumination device and a projection lens, having an arrangement for measuring the wavefront of the radiation traveling through the projection lens, wherein a device for varying the beam direction during the wavefront measurement is provided. The projection exposure apparatus can be designed in particular for operation at an operating wavelength of less than 15 nm (e.g. 13.5 nm), more particularly at an operating wavelength of less than 7 nm (e.g. 6.7 nm).

According to an embodiment, the illumination device has a field facet mirror having a plurality of field facets and a pupil facet mirror having a plurality of pupil facets, wherein the field facets are independently settable.

According to an embodiment, the device has a diffuser that is movable by way of rotation and/or translation.

According to an embodiment, the device has a beam direction control unit for the targeted control of the beam direction.

Further configurations of the invention can be gathered from the description and the dependent claims. The invention is explained in greater detail below on the basis of exemplary embodiments illustrated in the accompanying figures.

BRIEF DESCRIPTION OF THE DRAWINGS

In the figures:

FIGS. 1-2 show schematic illustrations for explaining the setup and functionality of an arrangement according to the invention for analysing the wavefront effect of an optical system in an exemplary embodiment, in which FIG. 1 shows the overall exemplary embodiment and FIG. 2 shows a representative channel for a representative illumination setting;

FIG. 4 shows exemplary intensity distributions, FIG. 5A shows an exemplary illumination setting, FIGS. 5B and 5C show corresponding illumination settings with modified illumination regions, and FIG. 5D shows corresponding shearograms.

DETAILED DESCRIPTION

Figure 1:
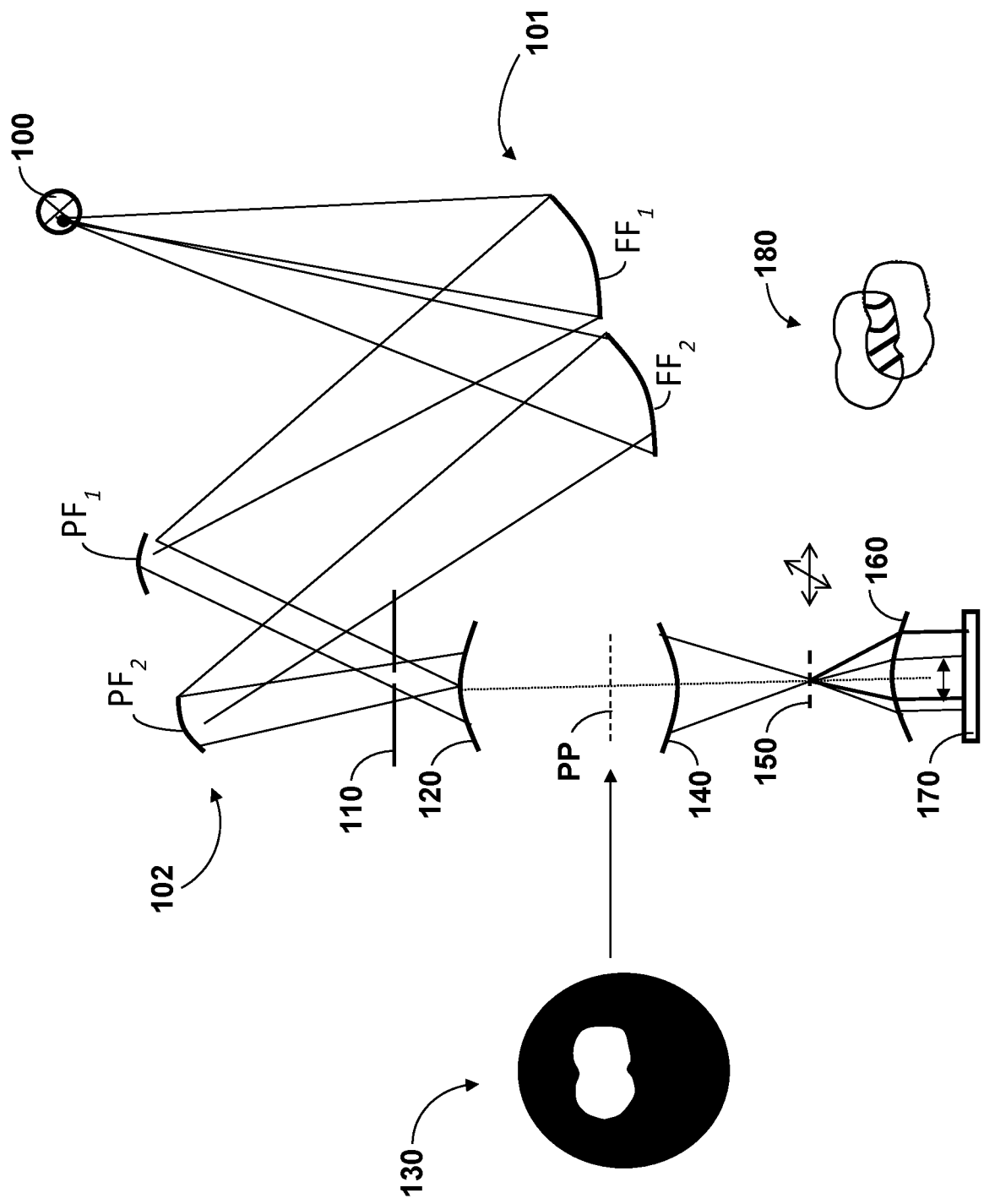

FIG. 1 shows a merely schematic illustration for explaining setup and functionality of an arrangement according to the invention for analyzing the wavefront effect of an optical system in an embodiment of the invention.

According to FIG. 1, light from a source point 100 of a spatially extensive and incoherent light source is initially incident on a field facet mirror 101 having a plurality of independently settable field facets, wherein, for the sake of simpler illustration, only two field facets $FF_1$ and $FF_2$ are shown in FIG. 1. From these field facets $FF_1$, $FF_2$, . . . , the light is incident, via a pupil facet mirror 102 (of which, again for the sake of simplicity, only two pupil facets $PF_1$ and $PF_2$ are shown), on a measurement mask designated "110." In a pupil plane PP, which is located downstream in the optical beam path, an intensity distribution 130 is produced in dependence on the angular distribution that is set via the field facets $FF_1$, $FF_2$, . . . of the field facet mirror 101. An interferogram, which is designated "180" in FIG. 1 and is captured by way of a detector 170, is produced by a diffraction grating 150, which is located downstream in the optical beam path. In FIG. 1, "120" furthermore symbolizes optical elements between the measurement mask 110 and a pupil plane PP, "140" symbolizes optical elements between the pupil plane PP and the diffraction grating 150, and "160" symbolizes optical elements between the diffraction grating 150 and the detector 170.

Figure 2:
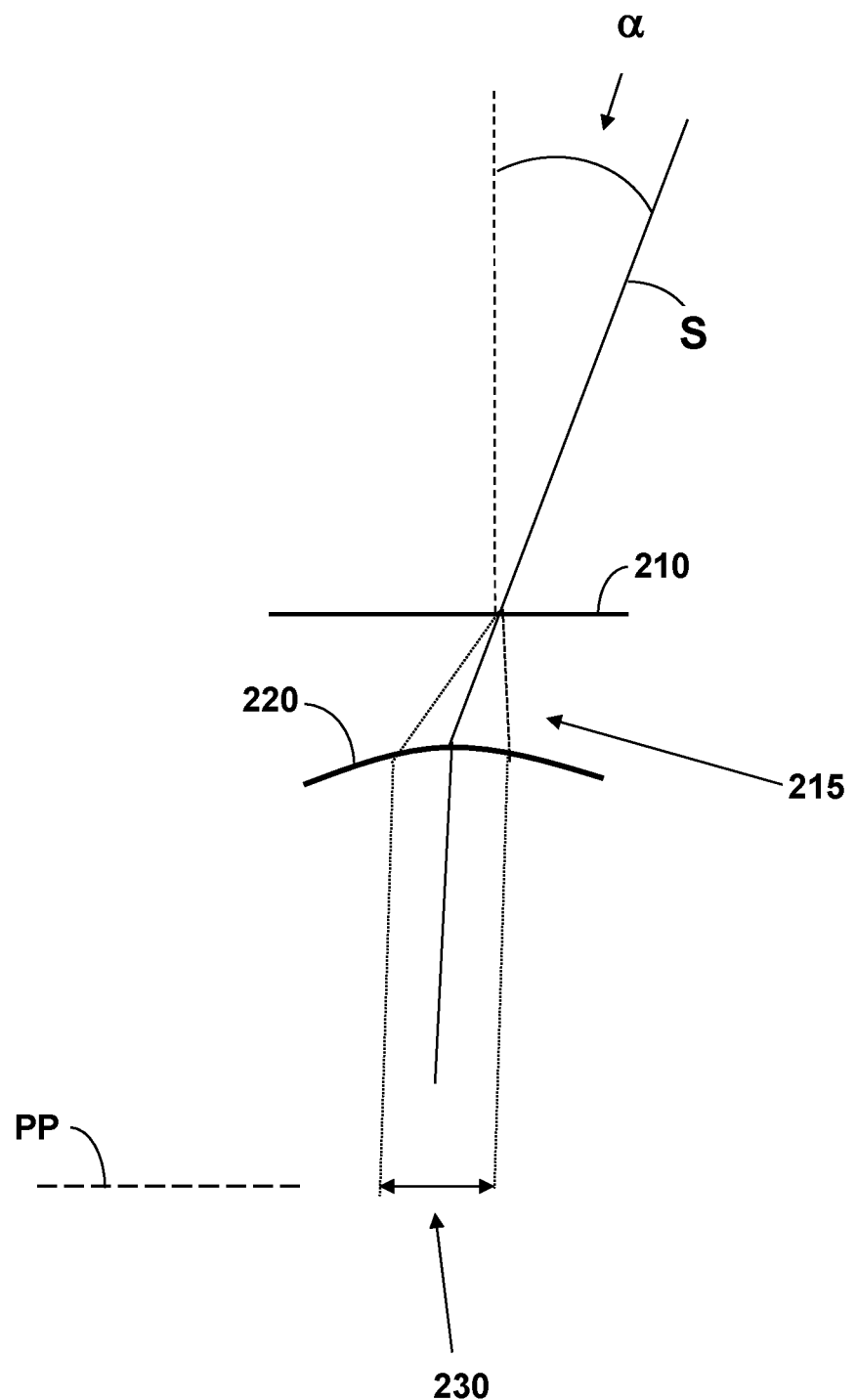

As is illustrated merely schematically in FIG. 2, the illumination of a measurement mask 210 at a specific angle α results in a corresponding scattering light cone 215 being produced, which in turn produces a region 230 that is illuminated in the pupil plane PP. In FIG. 2, optical elements between the measurement mask 210 and the pupil plane PP are symbolized by "220." By producing a multiplicity of such channels, it is possible to realize a desirable angular distribution and a corresponding illumination setting when illuminating the measurement mask 210.

In embodiments, it is also possible, as will be described below, for a suitable device to be used for realizing a—deterministic or random—variation of the beam direction of the light that is incident on the mirror arrangement or enters the optical system, with the aim of averaging out speckle patterns, which occur due to the spatial coherence of the incident light.

Figure 3A:
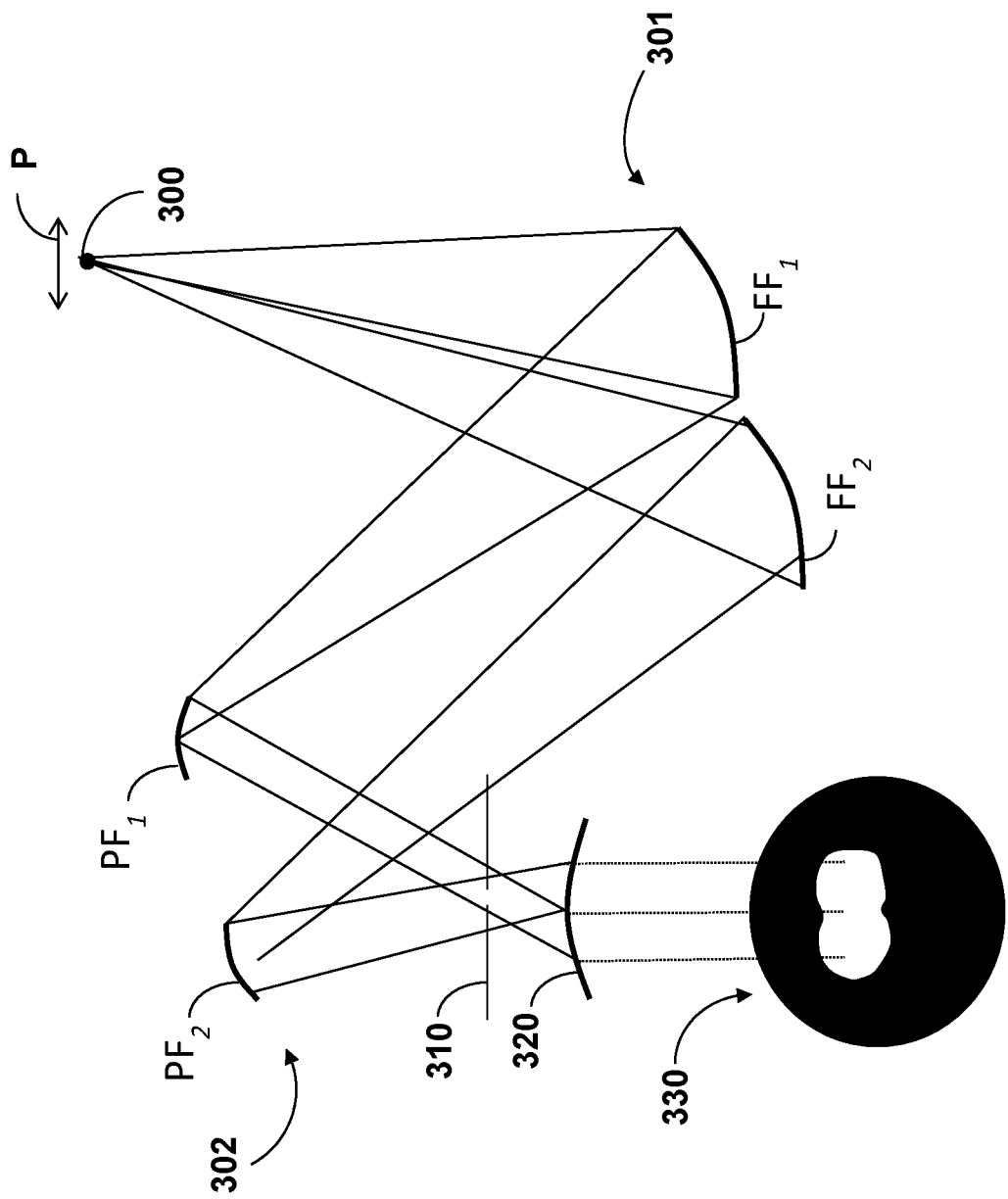
FIGS. 3A, 3B, 4, and 5A-5D show schematic illustrations for explaining further aspects and embodiments of the invention, in which FIG. 3A highlights lateral displacement of the illumination, FIG. 3B highlights use of a diffuser for the illumination.

FIG. 3A serves to illustrate this approach, wherein components that are analogous or substantially functionally identical in comparison with FIG. 1 are designated by reference numerals increased by "200." A lateral displacement of the source point 300, indicated in FIG. 3A by the double-headed arrow denoted "P," results in a lateral displacement of the pupil illumination. Coherent disturbances, which occur in the form of speckle patterns and thus have a random character, change in this case and can be reduced in the measurement result by way of averaging over a plurality of image recordings. The region that is illuminated in the pupil plane PP here migrates as a whole without a change in the relevant information relating to the wavefront deviations occurring.

Figure 3B:
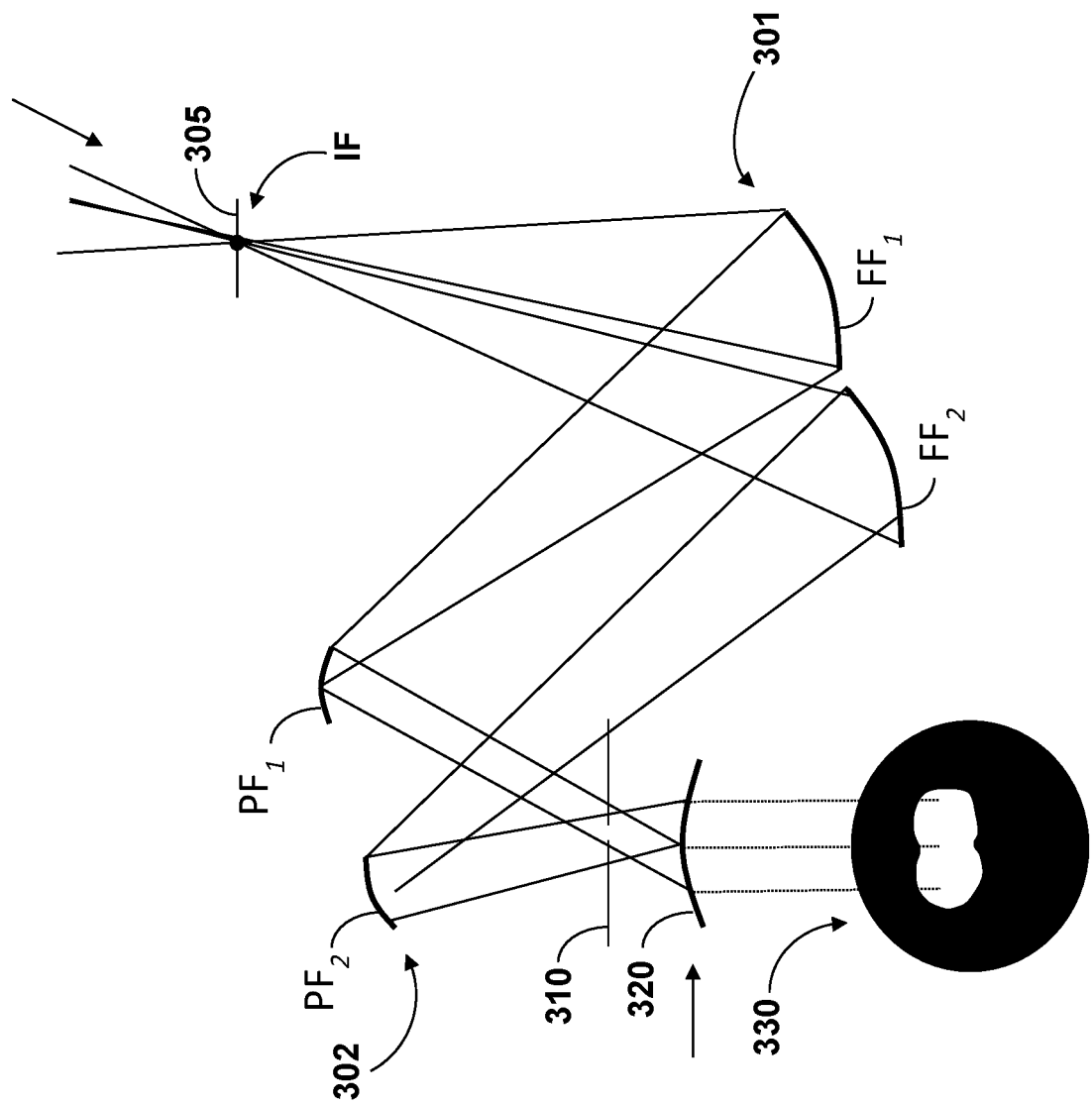

The aforementioned device for varying the beam direction can be for example a diffuser, which is moved by way of rotation and/or translation and is used in the region of the intermediate focus (IF) (for example a rotating EUV diffusing disk, which can be produced by FIB patterning of a thin SI membrane), as is indicated merely schematically in FIG. 3B. In a further embodiment, it is likewise possible to use a beam direction control unit, as is known from US 2005/0270511 A1, for the targeted or deterministic variation of the beam direction.

As will be explained below, the flexible setting of different illumination settings which is able to be realized in the arrangement according to the invention can also be used for absolute calibration.

Figure 4:
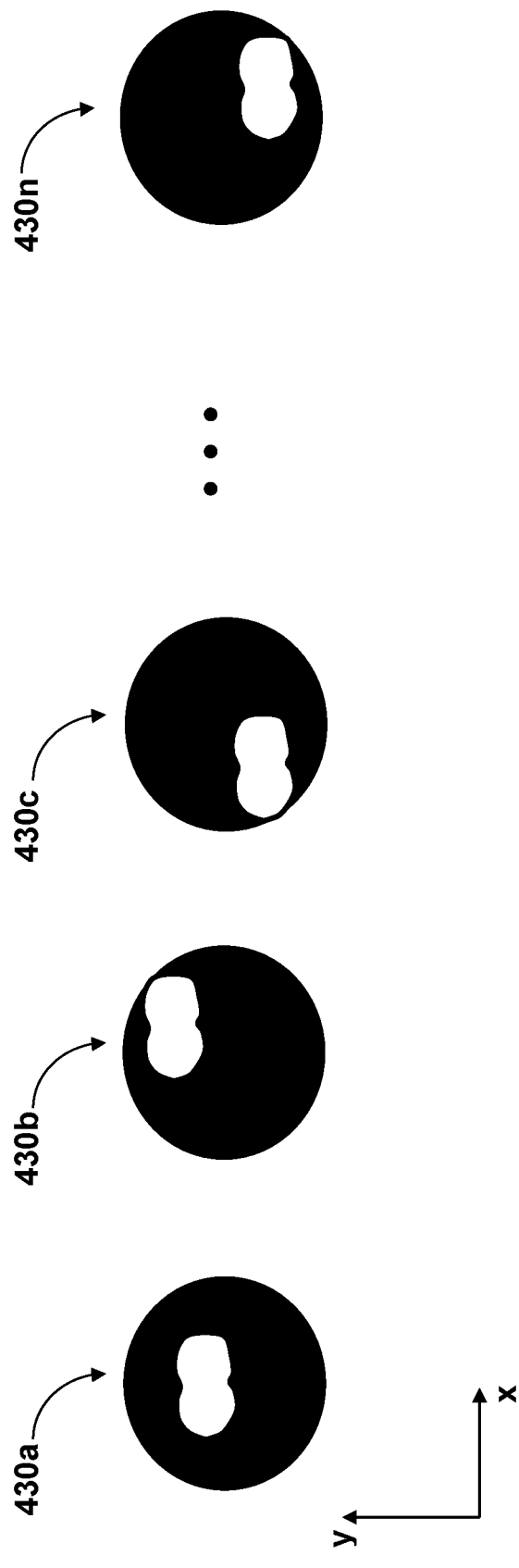

In embodiments, a plurality of interferograms can be captured in a plurality of measurement steps, wherein these measurement steps differ from one another in terms of the angular distribution of the illumination light that is incident on the measurement mask 110. FIG. 4 shows exemplary intensity distributions 430a, 430b, 430c, . . . , 430n set in the pupil plane. The invention now proceeds from the assumption that the systematic wavefront error of the measurement arrangement for each of these intensity distributions 430a, 430b, 430c, . . . , 430n matches. The wavefront deviations measured in a (pupil) region i can be represented as:

$$W_i = S^{Isotrop} + S_i^{Anisotrop} + POB_i \quad (1)$$

Here:
$W_i$ denotes the wavefront deviations, ascertained from at least two partial interferograms or shearograms, along the pupil region i
$S^{Isotrop}$ denotes the illumination-direction-independent portions of the systematic deviations of the measurement arrangement (shearing interferometer deviations);
$S_{Anisotrop}$ denotes the illumination-direction-dependent portions of the systematic shearing interferometer deviations, effective in the direction of the pupil region i; and
$POB_i$ denotes the system wavefront deviations of the optical system to be inspected (e.g. projection lens) in the pupil region i.

All of the aforementioned variables are indicated along a common coordinate system, e.g. along a Cartesian x-y-coordinate system around the region center.

The system wavefront deviations of the optical system to be inspected (e.g. of a projection lens) are decomposed into a portion that is common to all pupil regions and is obtained mathematically by averaging over all N pupil regions (i=1, . . . N) and the respective remaining differences in the pupil region no. i:

$$POB_i = \overline{POB_i} + (\Delta POB)_i \quad (2)$$

The component that is common to all pupil regions is referred to here and below as "basic portion." By inserting (2) into (1), the following is obtained:

$$W_i = S^{Isotrop} + S_i^{Anisotrop} + \overline{POB_i} + (\Delta POB)_i \quad (3)$$

By aggregating by region-independent and region-dependent variables, the following is obtained:

$$W_i = S^{Isotrop} + \overline{POB_i} S_i^{Anisotrop} + (\Delta POB)_i \quad (4)$$

The illumination-direction-dependent errors of the measurement arrangement (shearing interferometer error) can be partially avoided by way of concomitant rotation of the shearing interferometer during the pupil region selection. In this case, the shearing interferometer must be rotated as a whole, that is to say including the measurement mask and the detector. In such a procedure:

$$S_i^{Anisotrop}(\text{azimuthal angle}) = 0 \quad (5)$$

To avoid such concomitant rotation of the shearing interferometer, the anisotropic systematic shearing interferometer errors, that is to say those caused by shading effects, can be modeled by electromagnetic simulation calculations. This also applies when the illumination direction changes relative to the optical axis. Equation (4) can be described as:

$$W_i - S_i^{Anisotrop} = S^{Isotrop} + \overline{POB_i} + (\Delta POB)_i \quad (6)$$

wherein in equation (6), the known variables are found on the left and the unknown variables on the right. "Iterative stitching" of the variables, which are located on the left-hand side of equation (6) and are known over the N pupil regions, produces the superposition of the sought-for systematic shearing interferometer errors with the basic portion and the sought-for differences between the system wavefront and the basic portion.

In the last step, the basic portion is considered in more detail, because it disadvantageously superposes the sought-for systematic shearing interferometer errors. To estimate at least one basic portion component, a specific wavefront component of particular interest will be considered along the pupil below, for example a Z9. For such a component, is possible to mathematically calculate the basic portion by pupil partial region formation and averaging over the N partial regions. This basic portion has a specific characteristic over the partial region, that is to say can be considered to be a wavefront. This wavefront is fitted to the result of the aforementioned stitching ("stitching result 1") and then subtracted, which gives the sought-for systematic, isotropic shearing interferometer errors as absolute values. Hereby, the absolute calibration method for this wavefront component is complete. For other wavefront components that are to be ascertained, an analogous procedure may be used.

In further embodiments of the invention, the system wavefront measurement according to the invention can be performed at the same illumination setting that is also used in the actual microlithography process. In this way, it is possible to take account of the targeted illumination of specific pupil regions that typically takes place in the microlithography process, and the very system wavefront deviations that become effective in the microlithographic exposure can be captured in a targeted fashion. This will be described further below with reference to FIGS. 5A-5D.

Figure 5A:
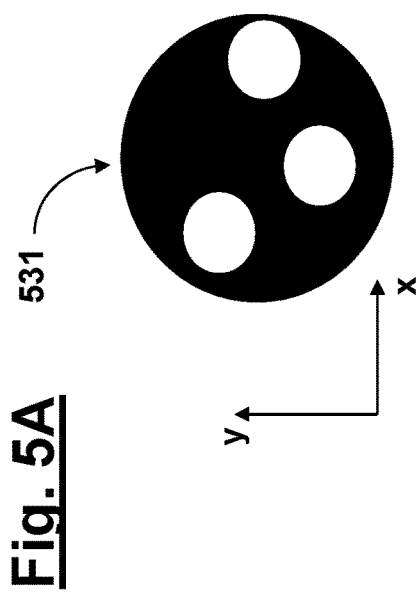
Figure 5B:
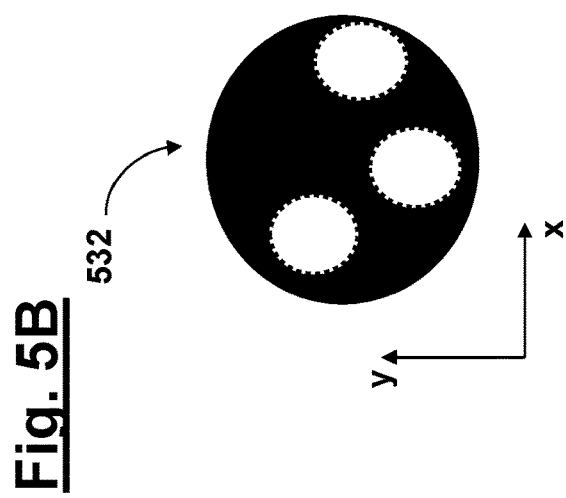
Figure 5C:
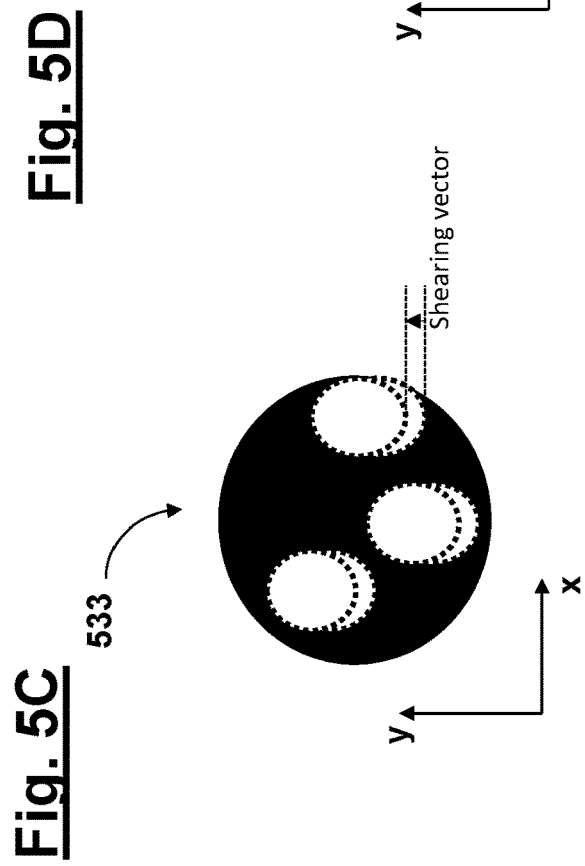
Figure 5D:
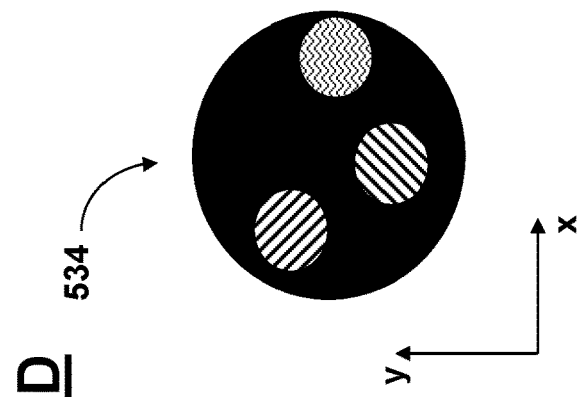

FIG. 5A initially shows an exemplary illumination setting, which is used in the microlithography process or should be set in a microlithographic projection exposure apparatus. According to FIG. 5B, a corresponding illumination setting, which substantially corresponds to that from FIG. 5A, but wherein the illumination poles are modified (i.e. "extended" in the shearing direction") such that the shearograms (FIG. 5D) ultimately obtained during the measurement are located as completely as possible in the regions shown in FIG. 5A, is set in the measurement arrangement according to the invention using the mirror arrangement according to the invention. In other words, the individual illuminated regions in the pupil are extended or expanded such that, after shearing, a sufficiently large overlap region, which coincides with the illumination setting, is present for the respectively sheared wavefronts according to FIG. 5D. For this reason, the illuminated regions in the pupil must, for a measurement at the exposure setting, be widened, viewed in the shearing direction, by the absolute value of the shearing, as is already indicated schematically in FIG. 5C.

Figure 6:
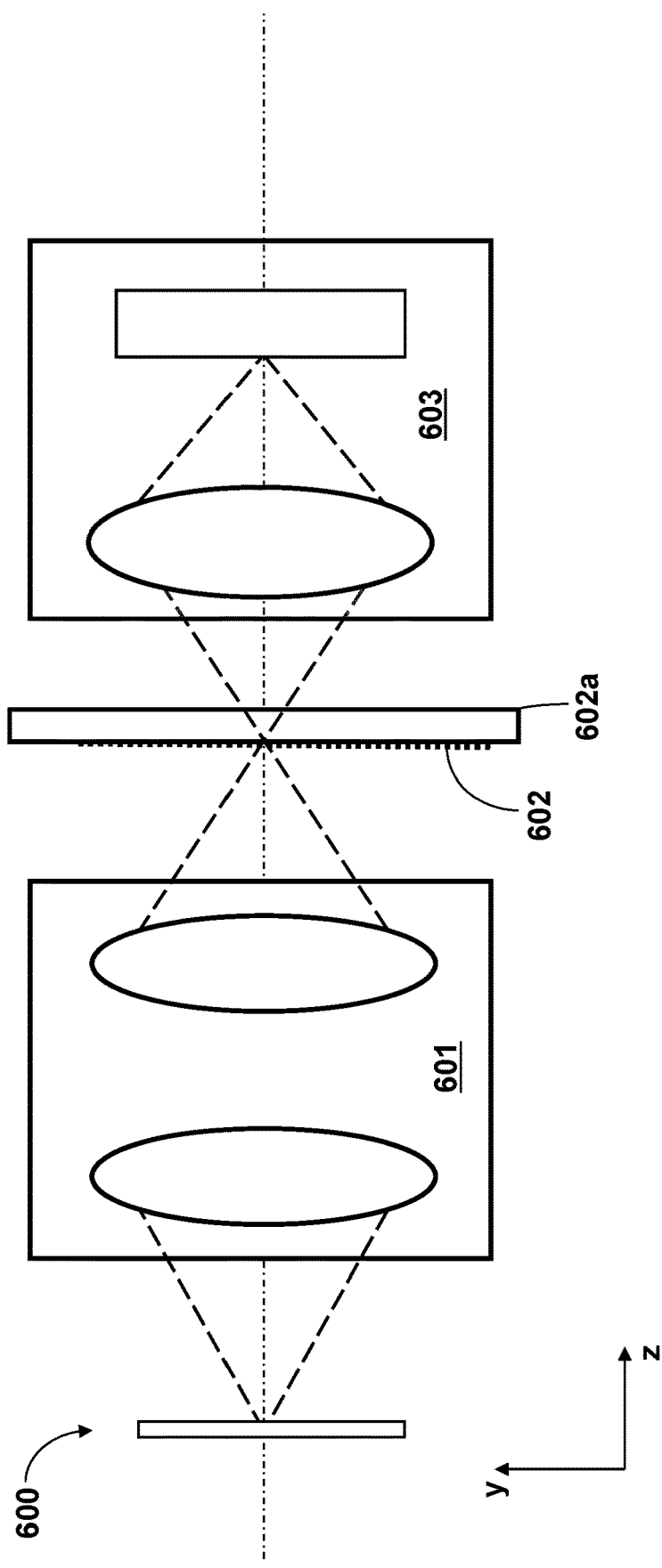
FIG. 6 shows a schematic illustration of an imaging optical unit provided with a representative basic setup of an apparatus for wavefront detection.

FIG. 6 shows in merely a schematic illustration the possible fundamental setup of an apparatus for wavefront detection.

In FIG. 6, an imaging optical unit that is to be checked with respect to its wavefront effect is denoted "601." This can also in particular be a projection lens or any desired partial system of an illumination device or of a projection lens of a microlithographic projection exposure apparatus. For checking the wavefront effect of said imaging optical unit 601 or for analyzing the wavefront of a light wave passing through said imaging optical unit 601, the arrangement in accordance with FIG. 1 has an illumination mask 600, through which light from a light source (not illustrated) enters the imaging optical unit 601 and is incident on a diffraction grating 602, arranged downstream of the imaging optical unit 601 in the light propagation direction (z-direction in the coordinate system shown), which diffraction grating 602 is provided on a substrate that is sufficiently transparent for light of the operating wavelength and is designated "620a." The light diffracted at the grating structure of the diffraction grating 602 into different orders of diffraction (e.g. 0, +1st and −1st order of diffraction) produces, in a (capturing) plane arranged downstream of the diffraction grating 602 with respect to the light propagation direction, an interference pattern, the evaluation of which in the case of a resolution by a camera-based sensor 603 in principle makes possible a wavefront analysis and thus allows a conclusion to be drawn relating to the optical effect or wavefront effect of the imaging optical unit 601 and for example an alignment of the optical components located in the imaging optical unit 601.

Even though the invention has been described on the basis of specific embodiments, numerous variations and alternative embodiments will be apparent to the person skilled in the art, for example through combination and/or exchange of features of individual embodiments. Accordingly, such variations and alternative embodiments are concomitantly encompassed by the present invention, and the scope of the invention is restricted only within the meaning of the appended patent claims and the equivalents thereof.

What is claimed is:

1. A method for analysing the wavefront effect of an optical system, comprising:
    illuminating a measurement mask with illumination light from an illumination device;
    producing an interferogram in a specified plane using a diffraction grating from a wavefront coming from the illuminated measurement mask and traveling through the optical system; and
    capturing the interferogram with a detector;
    wherein different angular distributions of the illumination light that is incident on the measurement mask are produced by a mirror arrangement of independently settable mirror elements;
    wherein a plurality of interferograms are captured in a plurality of measurement steps, wherein the measurement steps differ from one another in respective angular distribution of the illumination light that is incident on the measurement mask; and
    wherein a matching wavefront deviation portion in measurement results obtained respectively in the measurement steps is ascertained to determine respective system wavefront deviations of the optical system for pupil regions illuminated respectively in individual ones of the measurement steps.

2. The method as claimed in claim 1, further comprising: varying a beam direction of the illumination light that is incident on the mirror arrangement over time to at least partially average out speckle patterns.

3. The method as claimed in claim 1, wherein the optical system is a projection lens of a microlithographic projection exposure apparatus.

4. The method as claimed in claim 3, wherein the wavefront effect of the projection lens is ascertained in a targeted fashion for the pupil regions that are illuminated during operation of the projection exposure apparatus.

5. A method for analysing the wavefront effect of an optical system, comprising:
    illuminating a measurement mask with illumination light from an illumination device;
    producing an interferogram in a specified plane using a diffraction grating from a wavefront coming from the illuminated measurement mask and traveling through the optical system; and
    capturing the interferogram with a detector;
    wherein different angular distributions of the illumination light that is incident on the measurement mask are produced by a mirror arrangement of independently settable mirror elements;
    wherein the optical system is a projection lens of a microlithographic projection exposure apparatus; and
    wherein the wavefront effect of the projection lens is ascertained in a targeted fashion by setting the mirror arrangement for pupil regions which are illuminated during operation of the projection exposure apparatus.

6. The method as claimed in claim 5, wherein the optical system is configured to operate at an operating wavelength of less than 30 nm.

7. The method as claimed in claim 6, wherein the optical system is configured to operate at an operating wavelength of less than 15 nm.

8. An arrangement for analysing the wavefront effect of an optical system, comprising:
    an illumination device, having a field facet mirror with a plurality of field facets and having a pupil facet mirror with a plurality of pupil facets, wherein the field facets are independently adjustable to produce a desired angular distribution of illumination light;
    a measurement mask on which the illumination light is incident;
    a diffraction grating, which produces a plurality of interferograms in a specified plane from respective wavefronts, each of which, during the illumination of the measurement mask with the illumination light from the illumination device, comes from the illuminated measurement mask and travels through the optical system for different angular distributions of the illumination light that is incident on the measurement mask;
    a detector configured to capture the interferograms obtained for the different angular distributions of the illumination light that is incident on the measurement mask; and
    one or more processors configured to calculate the respective system wavefront deviations of the optical system for pupil regions that are respectively illuminated in individual ones of the measurement steps, from a matching wavefront deviation portion in the captured interferograms; and
    one or more memories configured to store the respective system wavefront deviations of the optical system.

9. The arrangement as claimed in claim 8, further comprising a device configured to vary a beam direction of the illumination light that is incident on the field facet mirror.

10. The arrangement as claimed in claim 9, wherein the device comprises a diffuser configured to move by rotation and/or by translation.

11. The arrangement as claimed in claim 9, wherein the device comprises a beam direction control unit configured to control the beam direction in a targeted manner.

12. The arrangement as claimed in claim 9, wherein the device is arranged in an intermediate focus located at an entrance of the illumination device.

13. The arrangement as claimed in claim 8, configured for installation into an optical system for microlithography.

14. The arrangement as claimed in claim 13, wherein the optical system for microlithography comprises an optical system of a microlithographic projection exposure apparatus.

15. The arrangement as claimed in claim 8, wherein the optical system is configured for operation at an operating wavelength of less than 30 nm.

16. The arrangement as claimed in claim 15, wherein the optical system is configured for operation at an operating wavelength of less than 15 nm.

17. A microlithographic projection exposure apparatus, designed for operation at an operating wavelength of less than 30 nm, comprising: an illumination device and a projection lens, and including an arrangement configured to measure a wavefront of radiation traveling through the projection lens and a device arranged at a region of intermediate focus at an entrance of the illumination device and configured to vary a beam direction of the radiation during the wavefront measurement.

18. The microlithographic projection exposure apparatus as claimed in claim 17, wherein the illumination device has a field facet mirror with a plurality of field facets ($FF_1$, $FF_2$, ... ) and has a pupil facet mirror with a plurality of pupil facets, wherein the field facets are configured to adjust independently of one another.

19. The arrangement as claimed in claim 17, wherein the device comprises a diffuser configured to move by rotation and/or by translation.

20. The arrangement as claimed in claim 17, wherein the device comprises a beam direction control unit controller configured to control the beam direction in a targeted manner.

* * * * *

UNITED STATES PATENT AND TRADEMARK OFFICE
CERTIFICATE OF CORRECTION

PATENT NO. : 11,426,067 B2
APPLICATION NO. : 16/830880
DATED : August 30, 2022
INVENTOR(S) : Rolf Freimann It is certified that error appears in the above-identified patent and that said Letters Patent is hereby corrected as shown below:

In the Specification

In Column 7, Line 21, delete "i" and insert -- i; --.

In Column 7, Line 25, delete "$S_{Anisotrop}$" and insert -- $S_i^{Anisotrop}$ --.

In Column 7, Line 46, delete "$W_i = S^{Isotrop} + S_i^{Anisotrop} + \overline{POB}_i(\Delta POB)_i$" and insert -- $W_i = S^{Isotrop} + S_i^{Anisotrop} + \overline{POB}_i + (\Delta POB)_i$ --.

In Column 7, Line 50, delete "$W_i = S^{Isotrop} + \overline{POB}_i S_i^{Anisotrop} + (\Delta POB)_i$" and insert -- $W_i = S^{Isotrop} + \overline{POB}_i + S_i^{Anisotrop} + (\Delta POB)_i$ --.

In the Claims

In Column 12, Line 14, in Claim 20, after "direction" delete "control unit".

Signed and Sealed this
Eleventh Day of July, 2023

Katherine Kelly Vidal
*Director of the United States Patent and Trademark Office*